United States Patent [19]
Dimaio et al.

[11] Patent Number: 6,054,474
[45] Date of Patent: Apr. 25, 2000

[54] HETEROCYCLIC COMPOUNDS FOR THE TREATMENT OF PAIN AND USE THEREOF

[75] Inventors: John Dimaio, Montreal; Dilip M. Dixit, Roxboro, both of Canada

[73] Assignee: Biochem Pharma, Inc., Laval, Canada

[21] Appl. No.: 08/981,932

[22] PCT Filed: Jul. 12, 1996

[86] PCT No.: PCT/CA96/00467

§ 371 Date: Mar. 25, 1998

§ 102(e) Date: Mar. 25, 1998

[87] PCT Pub. No.: WO97/03978

PCT Pub. Date: Feb. 6, 1997

[30] Foreign Application Priority Data

Jul. 14, 1995 [GB] United Kingdom .................... 9514417

[51] Int. Cl.[7] .......................... A01N 43/02; A01N 43/12; C07D 267/02; C07D 337/12
[52] U.S. Cl. .......................... 514/431; 514/443; 540/552; 549/12; 549/26; 549/43; 549/88; 549/90
[58] Field of Search .................................. 549/12, 26, 43, 549/88, 90; 540/552; 514/431, 443

[56] References Cited

U.S. PATENT DOCUMENTS 5,214,156  5/1993  Andersson et al. .......................... 549/75
5,637,624  6/1997  Schaus et al. ............................. 514/657

OTHER PUBLICATIONS

Malis et al., "animals Pharmacology of Wy–16,225, A New Analgesic Agent", The Journal of Pharmacology and Experimental Therapeutics, vol. 194, No. 3, pp. 488–498 (1975).

Fowler, C. et al., "$\mu$–,$\delta$,$\kappa$–Opioid Receptors and Their Subtypes. A Critical Review With Emphasis On Radioligand Binding Experiments," Neurochem. Int., vol. 24, No. 5, pp. 410–426 (1994).

Leslie, F.M., "Methods Used for the Study of Opioid Receptors," Pharma. Reviews, vol. 39, No. 3, pp. 197–249 (1987).

Lord, J.A.H., et al., "Endogenous opioid peptides: multiple agonist and receptors" Nature, vol. 267, pp. 495–499, (1977).

Martin, W.R., et al., "The Effects of Morphine– And Nalorphine–Like Drugs In The Nondependent and Morphine–Dependent Chronic Spinal Dog," Jour. of Pharma. and Exper. Therap., vol. 197, No. 3, pp. 517–532, (1976).

Raffa, R.B., et al., "Low Affinity of FMRFamide and Four FaRPs (FMRFamide–Related Peptides), Including the Mammalian–Derived FaRPs F–8–Famide (NPFF) and A–18–Famide, for Opioid $\mu$, $\delta$, $\kappa_1$, $\kappa_{2a}$, or $\kappa_{2b}$ Receptors," Peptides, vol. 15, No. 3, pp. 401–404, (1994).

Rothman, R.B., et al., "Interaction of Endogenous Opioid Peptides and Other Drugs with Four Kappa Opioid Binding Sites in Guinea Pig Brain," Peptides, vol. 11, pp. 311–331, (1990).

Siegmund, E. et al., "A Method for Evaluating both Non–Narcotic and Narcotic Analgesics," Proc. Soc. Ex. Biol. Med., vol. 95, pp. 729–731, (1957).

Downing, J.W., et al., "WY 16225 (Dezocine), A New Synthetic Opiate Agonist–Antogonist And Potent Analgesic: Comparison With Morphine For Relief Of Pain After Lower Abdominal Surgery," Anaesth., vol. 53, pp. 59–64 (1981).

Dunham N.W., et al., "A Note on a Simple Apparatus for Detecting Neurological Deficit in Rats and Mice," Jour. of the Amer. Pharma. Asso., vol. XLVI, No. 3, pp. 208–209, (1957).

Farooqui, A.A., et al., "Excitatory Amino Acid Receptors, Neural Membrane Phospholipid Metabolism and Neurological Disorder," Brain Res. Review, vol. 16 pp. 171–191, (1991).

Follenfant, R.L., et al., "Antinociceptive Effects of the Novel Opioid Peptide BW443C Compared with Classical Opiates; Peripheral Versus Central Actions," Br. J. Pharmacol. vol. 93, pp. 85–92, (1988).

Foster, A.C., et al., "Therapeutic Potential of NMDA receptor Antagonists As Neuroprotective Agents," Current and Fut. Trends in Anticonv. Anxiety, and Stoke Ther., pp. 301–329, (1990).

Fray, P.J., et al., "An Observational Method for Quantifying the Behavioural Effects of Dopamine Agonists: Contrasting Effects of d–Amphetamine and Apomorphine," Psychopharmacology, vol. 69, pp. 253–259 (1980).

(List continued on next page.)

Primary Examiner—Mukund J. Shah
Assistant Examiner—Tamthom N. Truong
Attorney, Agent, or Firm—Foley & Lardner

[57] ABSTRACT

Polycyclic alkaloids of formula (I),

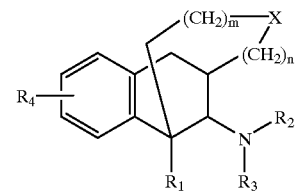

formula I wherein $R_1$ is H, $C_{1-6}$ alkyl, or $C_{6-12}$ aryl optionally substituted with polar groups; $R_2$ and $R_3$ are independently H, OH, $C_{1-6}$ alkyl, —C(NH)—NH$_2$, a positively charged group, or $C_{7-13}$ aralkyl optionally substituted with NH$_2$, OH, $C_{1-6}$ alkyl, or halogen; or $R_2$ and $R_3$ together form a 5 to 6 member ring optionally incorporating a heteroatom; $R_4$ is H, $C_{1-6}$ alkyl, OR$_6$, SR$_6$ or N(R$_6$)$_2$, wherein each $R_6$ is independently H, $C_{1-3}$ alkyl; X is O, S, SO, SO$_2$, N—R$_5$, or C—(R$_5$)$_2$, wherein each $R_5$ is independently H, $C_{1-6}$ alkyl, or $C_{7-13}$ aralkyl optionally interrupted with one or more heteroatom; n is an integer from 0 to 2; m is an integer from 0 to 3; with the proviso that when X is CH$_2$ then R1 is not CH$_3$, R$_2$ and R$_3$ are not both H, R$_4$ is not OH, m is not 3 and n is not 0. For the treatment of pain and pharmaceutically acceptable compositions comprising those compounds. The compounds of this invention acts as agonists at the opiate receptor.

20 Claims, 3 Drawing Sheets

OTHER PUBLICATIONS

Hughes, J., et al., "Effect of Morphine on Adrenergic Transmission in the Mouse Vas Deferens. Assessment of Agonist and Antagonist Potencies of Narcotic Analgesics," *Br. J. Pharmac.*, vol. 53, pp. 371–381, (1975).

Koek, W. et al., "Selective Blockade of N–Methyl–D–Aspartate (NMDA)–Induced Convulsions by NMDA Antagonists and Putative Glycine Antagonists: Relationship with Phencyclidine–Like Behavioral Effects," *The Jour. of Pharmac. and Exper. Thera.*, vol. 252, No. 1, pp. 349–357, (1990).

MacDermott, A.B., et al., "Receptors, Ion Channels and Synaptic Potentials Unerlying the Integrative Actions of Excitatory Amino Acids," *TINS*, vol. 10, No. 7, pp. 280–284, (1987).

Rogawski, M.a., et al., "Antiepileptic Drugs: Pharmacological Mechanisms and Clinical Efficacy with consideration of Promising Developmental Stage Compounds," *Pharma.*, vol. 42, No. 3, pp. 223–286 (1990).

Said, S.I., et al., "N–Methyl– D–Aspartate Receptors Outside The Central Nervous System: Activation Causes Acute Lung Injury That Is Mediated by Nitric Oxide Synthesis And Prevented By Vasoactive Intestinal Peptide," *Neuroscience*, vol. 65, No. 4, pp. 943–946, (1995).

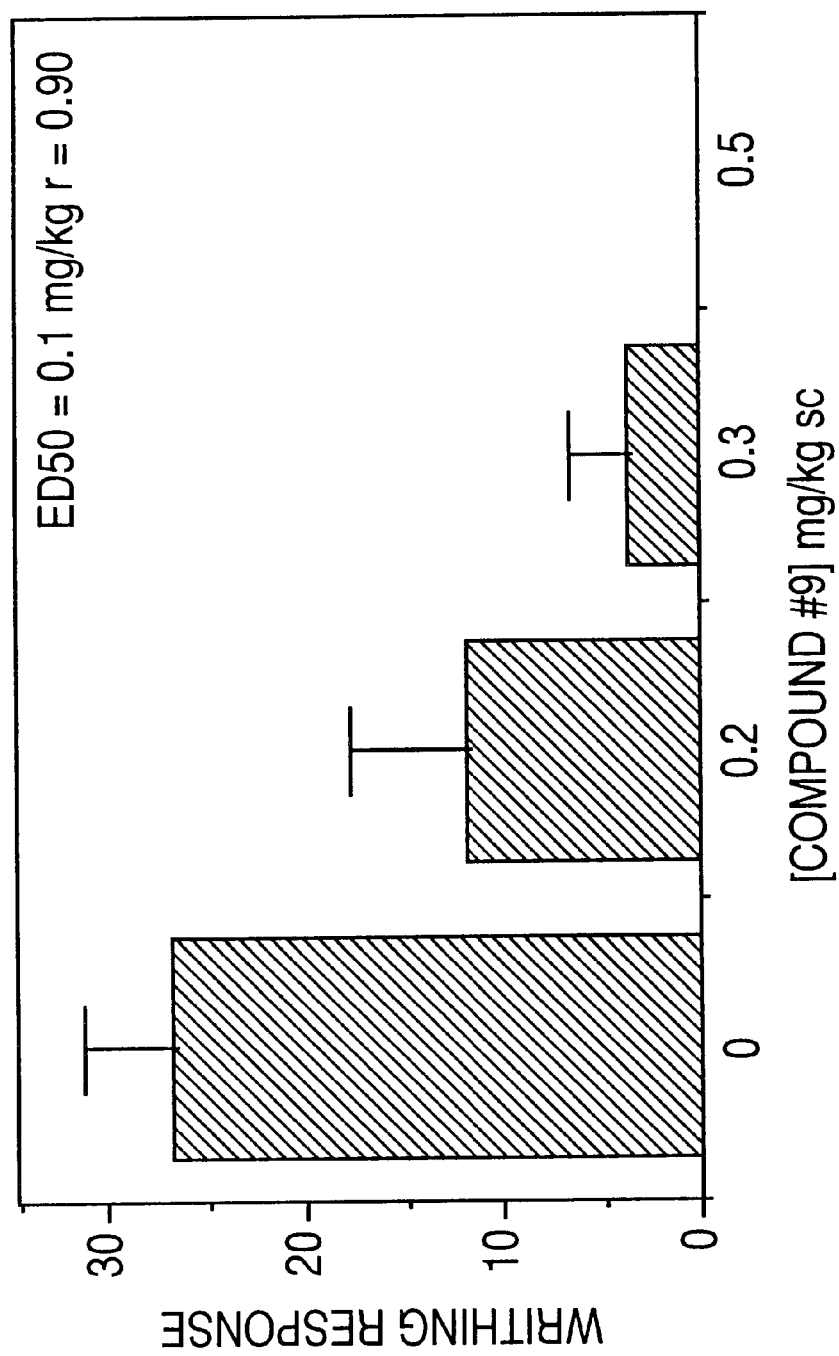

HETEROCYCLIC COMPOUNDS FOR THE TREATMENT OF PAIN AND USE THEREOF

FIELD OF THE INVENTION

The present invention relates to novel polycyclic opioid receptor agonists having analgesic activity and pharmaceutical acceptable compositions thereof. In another aspect, the invention relates to methods and uses relating to the novel agonists and compositions.

BACKGROUND OF THE INVENTION

Narcotic opiate analgesics remain the mainstay of presently available drug regimens used to alleviate moderate to severe pain. Opiate analgesics produce a characteristic antinociceptive response in various animal species (including homo sapiens) through activation of specific receptors in the central nervous system. It is well established that activation of one or more of these receptors produces antinociceptive effects in relevant animal models of pain assessment.

Multiple types of opioid receptors have been shown to co-exist in higher animals, of which at least three distinct classes have been characterized, with evidence for additional classes or subclasses: mu ($\mu$), kappa (K) and delta ($\delta$). For example, see W. Martin et al., *J. Pharmacol. Exp. Ther.*, 197, p. 517(1975); and J. Lord et al., *Nature* (London), 257, p. 495 (1977). The $\mu$ receptor is located in the brain and appears to be involved in the analgesic effect of morphine-like drugs. $\kappa$-Receptor activation in the brain and spinal cord appears capable of producing analgesia, particularly at the spinal level. The $\delta$-receptor is found in some peripheral tissues in addition to the brain and spinal cord, and shows a differentiating affinity for endogenous opioid peptides known as enkephalins. Finally, although it is doubtful that $\sigma$-receptors are strictly "opioid" in character as they are activated by non-opioid compounds, the majority of psychotomimetic effects of opioid drugs, such as dysphoria and hallucinations, appear to be mediated by this class of receptors.

SUMMARY Of THE INVENTION

The present invention provides for compounds having analgesic activity which are novel polycyclic opioid receptor agonists having the general structure represented by formula I.

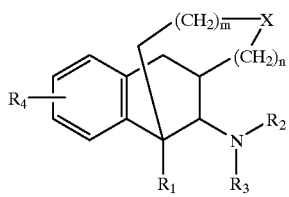

formula I wherein

R$_1$ is H, C$_{1-6}$ alkyl, or C$_{6-12}$ aryl optionally substituted with polar groups;

R$_2$ and R$_3$ are independently H, OH, C$_{1-6}$ alkyl, —C(NH)—NH$_2$, a positively charged group or C$_{7-13}$ aralkyl optionally substituted with NH$_2$, OH, C$_{1-6}$ alkyl, or halogen; or R$_2$ and R$_3$ together form a 5 to 6 member ring optionally incorporating a heteroatom;

R$_4$ is H, C$_{1-6}$ alkyl, OR$_6$, SR$_6$ or N(R$_6$)$_2$, wherein each R$_6$ is independently H, C$_{1-3}$ alkyl, or halogen;

X is O, S, SO, SO$_2$, or N—R$_5$, wherein each R$_5$ is independently H, C$_{1-6}$ alkyl, or C$_{7-13}$ aralkyl optionally interrupted with one or more heteroatom;

n is an integer from 0 to 2;

m is an integer frcm 0 to 3.

In another aspect of the present invention, there is provided a method of agonizing opioid receptors in a mammal comprising administering to said mammal an opioid receptor agonizing amount of a compound according to formula (I).

In a further aspect there is provide a method of inducing analgesia in a mammal comprising administering to said mammal a pharmaceutically effective amount of a compound according to formula (I).

It will be appreciated by those skilled in the art that the compounds of formula (I), depending on the substituents, may contain one or more chiral centers and thus exist in the form of many different isomers, optical isomers (i.e. enantiomers) and mixtures thereof including racemic mixtures. All such isomers, enantiomers and mixtures thereof including racemic mixtures are included within the scope of the invention.

The invention also provides for pharmaceutically acceptable compositions comprising compounds of formula (I), for use in the management of pain.

The invention also provides for pharmaceutically acceptable compositions comprising compounds of formula (I), for use as diagnostic aids and/or research tools such as radioligands, radiotracers with Positron Emission Tomography or paramagnetic agents for use with Magnetic Resonance Imaging for opiate receptor mediated processes.

The invention further provides the use of a compound of Formula (I) for the manufacture of therapeutic agents for the management of pain.

The invention further provides the use of a compound of Formula (I) for the manufacture of chemical compounds for use as diagnostic aids and/or research tools such as radioligands, radiotracers with Positron Emission Tomography or paramagnetic agents for use with Magnetic Resonance Imaging for opiate receptor mediated processes.

BRIEF DESCRIPTION OF FIGURES

FIG. 3 depicts dose dependent inhibition of the writhing response (PBQ) by compound #9 administered subcutaneously to mice.

DETAILED DESCRIPTION OF THE INVENTION

Figure 1:
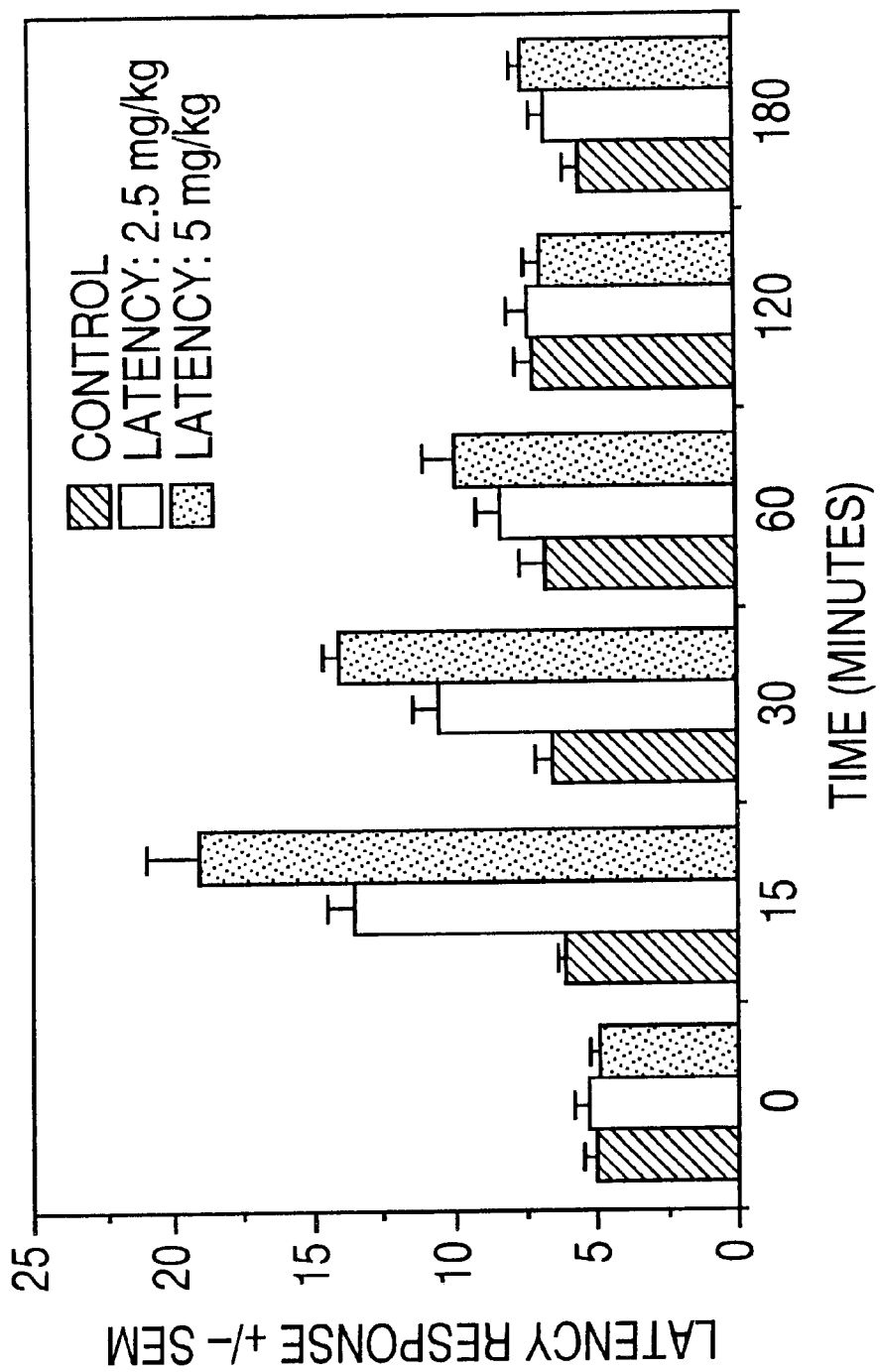
FIG. 1 indicates dose dependent inhibition of the latency response to radiant heat by compound #9 administered subcutaneously to mice.

The following common abbreviations are used throughout the specification and in the claims:

The term "ED$_{50}$" as shown in Table 1 for the PBQ writhing assay is defined as the dose of drug which induces a 50% reduction in the number of writhes observed compared to the control.

The term a "ED$_{50}$" used in the hot-plate assay (FIG. 1) is defined as the dose of drug required to increase the latency of response 2-fold compared to controls and was determined by log-probit analysis.

The term "K$_i$" is the binding inhibition constant. The term "K$_i^\delta$/K$_i^\mu$" is a value that may be used to measure selectivity.

This ratio represents the relationship of the affinities of compounds for binding to the μ- and δ-receptors.

As used in this application, the term 'alkyl' represents a saturated or unsaturated, substituted (by a halogen, hydroxyl, amino, or $C_{6-20}$ aryl) or unsubstituted; straight chain, branched chain, or cyclic hydrocarbon moiety wherein said straight chain, branched chain, or cyclic hydrocarbon moiety can be interrupted by one or more heteroatoms (such as oxygen, nitrogen or sulfur).

The term "heteroatom" as used hereinafter represents N, O and S as well as SO and $SO_2$.

The term 'aryl' represents a carbocyclic moiety which may be substituted (e.g. $C_{1-6}$ alkyl, halogen, hydroxyl, amino), interrupted by at least one heteroatom (e.g., N, O or S) and containing at least one benzenoid-type ring (e.g. phenyl and naphthyl).

The term 'aralkyl' represents an aryl group attached to the adjacent atom by an alkyl (e.g. benzyl).

The compounds of the present invention are represented by Formula (I) as defined above.

Preferably, $R_1$ is cyclohexyl.

Preferably, $R_1$ is phenyl optionally substituted with polar groups.

Preferred polar groups are COOH, $NH_2$ or guanidine.

More preferably, $R_1$ is H.

Most preferably, $R_1$ is $CH_3$.

Preferably, $R_2$ is H.

Preferably, $R_3$ is OH.

Most preferably, $R_3$ is H.

Preferably, $R_4$ is $OCH_3$.

Preferably, $R_4$ is OH.

Preferably, X is NH.

More preferably, X is O.

Most preferably, X is S.

Preferably, $R_5$ is $C_{1-6}$ alkyl.

More preferably, $R_5$ is $CH_3$.

Most preferably, $R_5$ is H.

Preferably, n is 0.

Preferably, m is 3.

A preferred compound of the invention includes:

Compound #8b: 5,6,7,8,9,11,12-heptahydro-3-methoxy-5-methyl-10-thia-5,11-methanobenzocyclodecene-13-amine.

A preferred compound of the invention includes:

Compound #9: 5,6,7,8,9,11,12-heptahydro-3-hydroxy-5-methyl-10-thia-5,11-methanobenzocyclodecen-13-amine (sulphazocine).

A preferred compound of the invention includes:

Compound #10: 5,6,7,8,9,11,12-heptahydro-3-hydroxy-5-methyl-10-thia-5,11-methanobenzocyclodecene-13-hydroxylamine.

A preferred compound of the invention includes:

Compound #9a (−)-trans-5,6,7,8,9,11,12-heptahydro-10-thia-3-hydroxy-5-methyl-5,11-methanobenzocyclodecen-13-amine;

A preferred compound of the invention includes:

Compound #11 trans-5,6,7,8,9,11,12-heptahydro-10-thia-3-hydroxy-5-methyl-5,11l-methanobenzocyclodecen-13-guanidine A preferred compound of the invention includes:

Compound #12 trans-5,6,7,8,9,11,12-heptahydro-10-sulphono-3-hydroxy-5-methyl-5,11-methanobenzocyclo-decen-13-amine More preferred compounds of the invention include:

Compound #9: 5,6,7,8,9,11,12-heptahydro-3-hydroxy-5-methyl-10-thia-5,11 methanobenzocyclodecen-13-amine (sulphazocine); and compound #10: 5,6,7,8,9,11,12-heptahydro-3-hydroxy-5-methyl-10-thia-5,11-methanobenzocyclodecene-13-hydroxylamine;

Most preferred compound of the invention include:

Compound #9: 5,6,7,8,9,11,12-heptahydro-3-hydroxy-5-methyl-10-thia-5,11-methanobenzocyclodecen-13-amine (sulphazocine); and compound #9a (−)-trans-5,6,7,8,9,11,12-heptahydro-thia-3-hydroxy-5-methyl-5,11-methanobenzocyclodecen-13-amine.

The preferred compounds of the present invention can be synthesized using conventional preparative steps and recovery methods known to those skilled in the art of organic and bio-organic synthesis, while providing new and unique combinations for the overall synthesis of each compound. Preferred synthetic routes for intermediates involved in the synthesis as well as the resulting compounds of the present invention follow. Successful preparation of these compounds is possible by way of several synthetic routes one of which is outlined in Scheme 1.

SCHEME 1

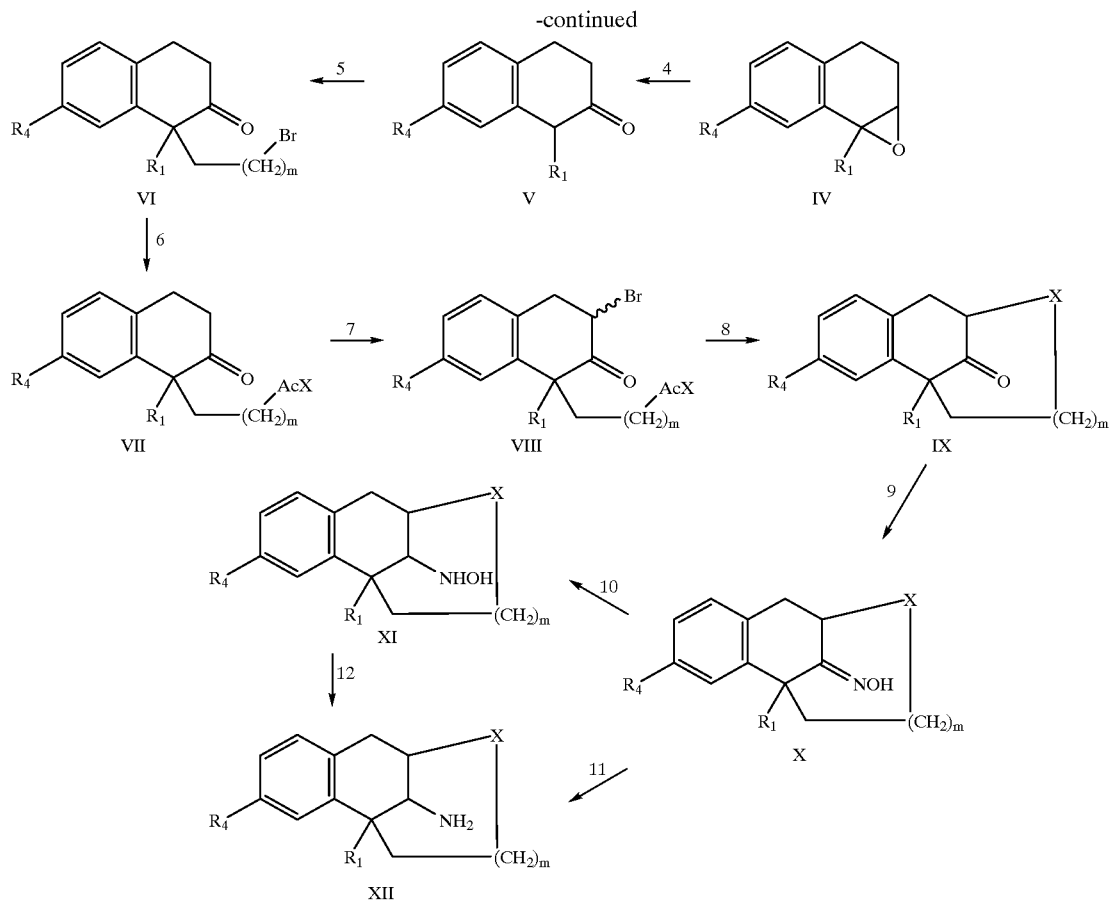

The steps illustrated in Scheme 1 can be briefly described as follows:

Step 1:
Compound I, an alkyl-1-tetralone, is treated with an appropriate Grignard Reagent such as methyl magnesium bromide in a dry non-polar solvent such as THF, to generate the tertiary alcohol, Compound II.

Step 2:
The alcohol, Compound II is dehydrated under acidic conditions, such as aqueous saturated $NH_4Cl$, to yield Compound III.

Step 3:
The double bond at position 1 on the olefin is epoxidized using standard reagents and solvents, such monoperoxyphthalic acid magnesium salt in isopropanol, to produce the epoxide, Compound IV.

Step 4:
The epoxide is rearranged under acidic conditions, such as aqueous $NaHCO_3$, using standard techniques to generate the ketone, Compound V.

Step 5:
Alkylation of the bis-alkyl-2-tetrone (Compound V) is accomplished under basic conditions in non-polar solvent using a dihaloalkyl reagent, such as dibromobutane, to yield Compound VI.

Step 6:
Nucleophilic displacement of bromide is accomplished with an appropriate acylating agent, such as potassium thiacetate to produce Compound VII.

Step 7:
The 3 position of the acylated tetralone (Compound VII) is halogenated in a non-polar solvent, such as a mixture of benzene and dry THF, using an appropriate reagent and non-polar solvent such as Bromine in dry THF to generate Compound VIII.

Step 8:
The side chain is cyclized under basic conditions using standard reagents and solvents such as lithium bromide and dry THF under Argon, with the addition of a base such as sodium methoxide, generating the polycyclic compound (Compound IX).

Step 9:
The ketone group of compound IX is converted to an alkyloxime using standard procedures well known in the art affording compound X.

Steps 10 and 11:
Compound X is reduced using a Borane-THF complex. If conducted in THF, a 50:50 mixture of compounds XI and XII is obtained. If the reaction is conducted in diglyme (2-methoxyethyl ether), the amine, (Compound XII) is selectively produced.

Step 12:
Compound XI can be recycled and reduced to the amine using a Borane-THF complex conducted in diglyme to yield Compound XII.

It is also appreciated that the compounds of the present invention can be modified by one skilled in the art in such a manner as to attach labels such as radioactive labels enabling detection of the compound for use as a radiotracer. The compounds of the present invention may be used as agonists at the opiate receptor in vitro or ex vivo as in the case of radio-labeling agents, radiotracers for use with Positron Emission Tomography, paramagnetic agents for use in Magnetic Resonance Imaging, and NMDA receptor-linked calcium channel antagonists.

It is appreciated that the compounds of the present invention can be modified by one skilled in the art in such a manner as to prevent access into the central nervous system such that they can function as opiate receptor agonists in peripheral tissues.

The present invention also provides pharmaceutical compositions which comprise a pharmaceutically effective amount of the compounds of this invention, or pharmaceutically acceptable salts thereof, and, preferably, a pharmaceutically acceptable carrier or adjuvant. The term "pharmaceutically effective amount" is the amount of compound required upon administration to a mammal in order to induce analgesia. Also, the term "opioid receptor agonizing amount" refers to the amount of compound administered to a mammal necessary to bind and/or activate opioid receptors in vivo.

Therapeutic methods of this invention comprise the step of treating patients in a pharmaceutically acceptable manner with those compounds or compositions. Such compositions may be in the form of tablets, capsules, caplets, powders, granules, lozenges, suppositories, reconstitutable powders, or liquid preparations, such as oral or sterile parenteral solutions or suspensions.

The therapeutic agents of the present invention may be administered alone or in combination with pharmaceutically acceptable carriers. The proportion of each carrier is determined by the solubility and chemical nature of the compound, the route of administration, and standard pharmaceutical practice.

In order to obtain consistency of administration, it is preferred that a composition of the invention is in the form of a unit dose. The unit dose presentation forms for oral administration may be tablets and capsules and may contain conventional excipients. For example, binding agents, such as acacia, gelatin, sorbitol, or polyvinylpyrolidone; fillers, such as lactose, sugar, maize-starch, calcium phosphate, sorbitol or glycine; tabletting lubricants such as magnesium stearate; disintegrants, such as starch, polyvinylpyrrolidone, sodium starch glycollate or microcrystalline cellulose; or pharmaceutically acceptable wetting agents such as sodium lauryl sulphate.

The compounds may be injected parenterally; this being intramuscularly, intravenously, or subcutaneously. For parenteral administration, the compound may be used in the form of sterile solutions containing other solutes, for example, sufficient saline or glucose to make the solution isotonic.

The compounds may be administered orally in the form of tablets, capsules, or granules containing suitable excipients such as starch, lactose, white sugar and the like. The compounds may be administered orally in the form of solutions which may contain coloring and/or flavoring agents. The compounds may also be administered sublingually in the form of tracheas or lozenges in which each active ingredient is mixed with sugar or corn syrups, flavoring agents and dyes, and then dehydrated sufficiently to make the mixture suitable for pressing into solid form.

The solid oral compositions may be prepared by conventional methods of blending, filling, tabletting, or the like. Repeated blending operations may be used to distribute the active agent throughout those compositions employing large quantities of fillers. Such operations are, of course, conventional in the art. The tablets may be coated according to methods well known in normal pharmaceutical practice, in particular with an enteric coating.

Oral liquid preparations may be in the form of emulsions, syrups, or elixirs, or may be presented as a dry product for reconstitution with water or other suitable vehicle before use. Such liquid preparations may or may not contain conventional additives. For example suspending agents, such as sorbitol, syrup, methyl cellulose, gelatin, hydroxyethylcellulose, carboxymethylcellulose, aluminum stearate gel, or hydrogenated edible fats; emulsifying agents, such as sorbitan monooleate or acaci; non-aqueous vehicles (which may include edible oils), such as almond oil, fractionated coconut oil, oily esters selected from the group consisting of glycerine, propylene glycol, ethylene glycol, and ethyl alcohol; preservatives, for instance methyl para-hydroxybenzoate, ethyl para-hydroxybenzoate, n-propyl parahydroxybenzoate, or n-butyl parahydroxybenzoate of sorbic acid; and, if desired, conventional flavoring or coloring agents.

For parenteral administration, fluid unit dosage forms may be prepared by utilizing the compound and a sterile vehicle, and, depending on the concentration employed, may be either suspended or dissolved in the vehicle. Once in solution, the compound may be injected and filter sterilized before filling a suitable vial or ampoule and subsequently sealing the carrier or storage package. Adjuvants, such as a local anesthetic, a preservative or a buffering agent, may be dissolved in the vehicle prior to use. Stability of the pharmaceutical composition may be enhanced by freezing the composition after filling the vial and removing the water under vacuum, (e.g., freeze drying the composition). Parenteral suspensions may be prepared in substantially the same manner, except that the compound should be suspended in the vehicle rather than being dissolved, and, further, sterilization is not achievable by filtration. The compound may be sterilized, however, by exposing it to ethylene oxide before suspending it in the sterile vehicle. A surfactant or wetting solution may be advantageously included in the composition to facilitate uniform distribution of the compound.

The pharmaceutical compositions of this invention comprise a pharmaceutically effective amount of a compound of this invention and a pharmaceutically acceptable carrier.

Typically, they contain from about 0.1% to about 99% by weight, preferably from about 10% to about 60% by weight, of a compound of this invention, depending on which method of administration is employed.

The present invention also provides a method for management of pain in patients, such as mammals, including humans, which comprises the step of administering to the patient a pharmaceutically effective amount of a compound, a pharmaceutically acceptable salt thereof, or a pharmaceutical composition as described above.

Physicians will determine the dosage of the present therapeutic agents which will be most suitable. Dosages may vary with the mode of administration and the particular compound chosen. In addition, the dosage may vary with the particular patient under treatment. The dosage of the compound used in the treatment will vary, depending on the seriousness of the disorder, the weight of the patient, the relative efficacy of the compound and the judgment of the treating physician. Such therapy may extend for several weeks, in an intermittent or uninterrupted manner, until the patient's symptoms are eliminated.

A number of heterocyclic compounds based on the general formula I, have been prepared and evaluated as opioid receptor agonists. These compounds are listed in Table 1 along with their respective binding inhibition constants and inhibitory activity in the PBQ assay. These results indicate that the compounds of the invention are effective as analgesic agents.

The compounds of the present invention may be used as opiate receptor agonists in vitro or ex vivo as in the case of, for example, radio-labeling agents, radiotracers, paramagnetic agents. The compounds of the invention may be used as research tools and/or diagnostic aids.

For preparation of the compounds of this invention, various methods can be employed depending upon the particular starting materials and/or intermediates involved. Successful preparation of these compounds is possible by way of several synthetic routes some of which are outlined below.

To further assist in understanding the present invention, the following non-limiting examples of such opiate receptor agonist compounds are provided. The following examples, of course, should not be construed as specifically limiting the present invention, variations presently known or later developed, which would be within the purview of one skilled in the art and considered to fall within the scope of the present invention as described herein.

EXAMPLE 1

Preparation of 1,2-dihydro-7-methoxy-4-methylnaphthalene

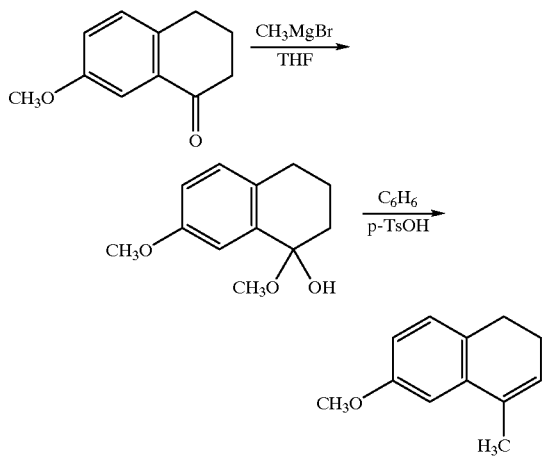

7-methoxy-1-tetralone (25 g) was dried via azeotropic distillation of toluene and dissolved in dried THF (200 ml). The solution was cooled at −70° C. (under Ar and methyl magnesium bromide (1.4 M in toluene/THF, 187.5 ml) was added. The combined reaction mixture was allowed to stir at ambient temperature overnight. It was carefully treated with aqueous saturated $NH_4Cl$ and extracted with ethylacetate. The latter solution was washed with brine, dried over $MgSO_4$ and evaporated. The residue was dissolved in benzene (150 ml), p-TSOH (0.1 g) was added and the mixture was heated to reflux using a Dean-Stark condenser until the dehydration reaction was complete. This benzene solution was diluted with ethylacetate, washed with $NaHCO_3$, dried over $MgSO_4$ and evaporated. The residue was extracted with hexanes, passed through a silica gel column and eluted with a mixture of hexanes and ethylacetate (1:0, 400:1, 200:1). The yield of the product was 20.87 g (84.42%).

$^1$H NMR (300 MHz, $CDCl_3$) δ: 2.05 (s, 3H); 2.23 (m, 2H); 2.69 (t, 2H); 3.81 (s, 3H) 5.88 (m, 1H); 6.68–7.06 (m, 3H) ppm.

EXAMPLE 2

Preparation of 7-methoxy-1-methyl-2-tetralone

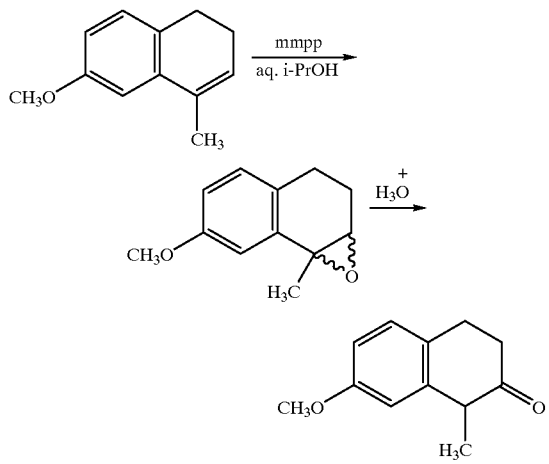

Dihydro-7-methoxy-4-methylnaphthalene (20.87 g) was dissolved in isopropanol (100 ml) and cooled in an ice bath. Monoperoxyphthalic acid magnesium salt (mmpp) (17 g) was added, then water (50 ml) was added and the mixture was stirred at room temperature for 2 hours. When oxidation was complete, the product mixture was hydrolyzed with aqueous $NaHCO_3$, partially evaporated and extracted with ethylacetate. The latter extract was washed with brine and evaporated. The residue was dissolved in a mixture of ethanol (156 ml), water (121 ml) and conc. $H_2SO_4$ (24.3 ml), and heated to reflux under $N_2$ atmosphere for 3 hours, cooled and neutralized with $NaHCO_3$. After partial evaporation, the residue was extracted with ethylacetate, washed with brine, dried over $MgSO_4$ and evaporated. The product was purified on a silica gel column using a mixture of hexanes and ethylacetate (100:1, 50:1, 50:1.5). The yield of the product was 16.2 g (71%).

$^1$H NMR (300 MHz, $CDCl_3$) δ: 1.47 (d, 3H); 2.55 (m, 2H); 3.02 (m, 2H); 3.5 (m, 1H); 3.81 (s, 3H); 6.75–6.77 (m, 3H) ppm. IR (film) 1714 $cm^{-1}$.

EXAMPLE 3

Preparation of 1-(4'-bromobutyl)-1-methyl-7-methoxy-2-tetralone

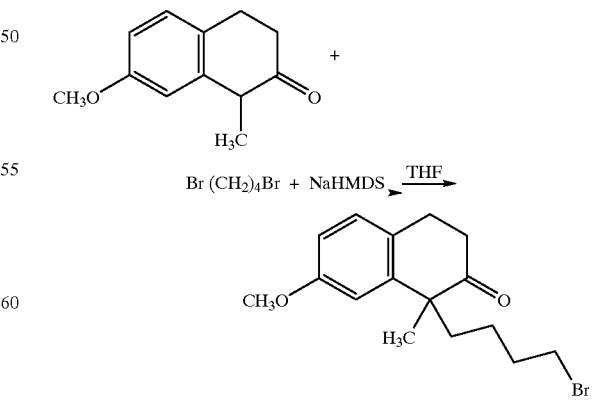

7-Methoxy-1-methyl-2-tetralone (4 g) was dried via azeotropic distillation of toluene, dissolved in dry THF (150 ml), cooled in an ice bath under Ar atmosphere and sodium bis (trimethylsilyl) amide solution (NaHMDS)(1 M in THF, 23.13 ml) was added and stirred for ½ hour. 1,4-Dibromobutane (9.78 ml) was added and the reaction mixture was allowed to warm up to room temperature overnight, after which it was hydrolyzed with brine, extracted with ethylacetate, dried over MgSO$_4$ and evaporated. The product mixture was purified on a silica gel column using a mixture of hexanes and ethylacetate (200:1, 150:1,100:1, 75:1 and 50:1). The yield of the product was 5.19 g (76%).

$^1$H NMR: (300 MHz, CDCl$_3$) δ: 1.09 (m, 2H); 1.37 (s, 3H) 1.71 (m, 3H); 2.1 (m, 3H); 2.68 (m, 2H); 2.97 (m, 2H); 3.26 (t, 2H); 3.8 (s, 3H), 6.72–7.09 (m, 3H) ppm.

EXAMPLE 4

Preparation of 1-(4'-acetothiobutyl)-1-methyl-7-methoxy-2-tetralone

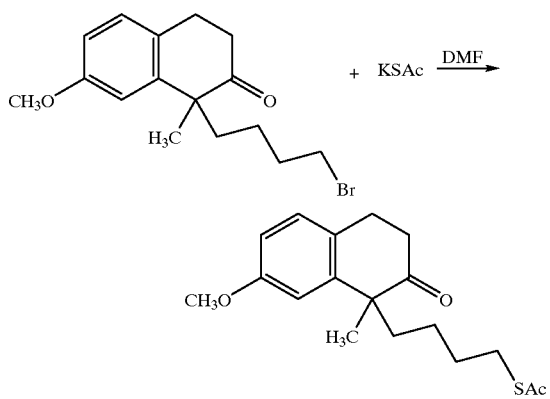

1-(4'-Bromobutyl)-1-methyl-7-methoxy-2-tetralone (4.48 g) was dried via azeotropic distillation of toluene and dissolved in dry DMF (25 ml). Potassium thiacetate (5.86 g) was added and the mixture was allowed to stir under Ar atmosphere overnight, after which it was extracted with ethylacetate, washed with brine, dried over MgSO$_4$ and evaporated. The residue was purified on a silica gel column using a mixture of hexanes and ethylacetate (75:1, 50:1, 20:1). The yield of the product was 3.9 g (88.3%).

$^1$H NMR (300 MHz, CDCl$_3$) δ: 0.99 (m, 2H); 1.5 (m, 6H); 2.07 (m, 1H); 2.25 (s, 3H); 2.65 (m, 4H); 2.95 (m, 2H); 3.79 (s, 3H); 6.71–7.08 (m, 3H) ppm.

EXAMPLE 5

Preparation of an epimeric mixture of 3-bromo-1-(4'-acetothiobutyl)-1-methyl-7-methoxy-2-tetralone

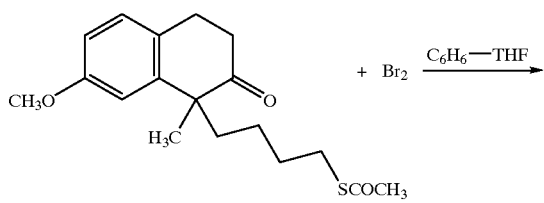

-continued

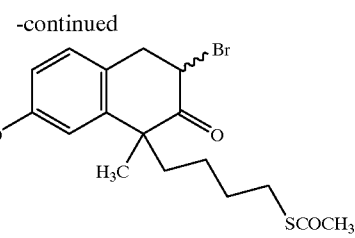

1-(4'-Acetothiobutyl)-1-methyl-7-methoxy-2-tetralone (4 g) was dried via azeotropic distillation of toluene. It was dissolved in a mixture of benzene (244 ml) and dry THF (64 ml) and stirred at room temperature under Ar atmosphere. Bromine (0.8 ml) was dissolved in dry THF (26 ml) and gradually added to the reaction mixture under Ar flow. After 1 hour of stirring, the product mixture was hydrolyzed with aqueous NaHCO$_3$, extracted with ethylacetate, washed with brine, dried over MgSO$_4$ and evaporated. The residue was dried via azeotropic distillation of toluene and then dried further under high vacuum.

EXAMPLE 6

Preparation of 5,6,7,8,9,11,1-heptahydro-3-methoxy-5-methyl-10-thia-5,11-ethano benzocyclodecen-13-one

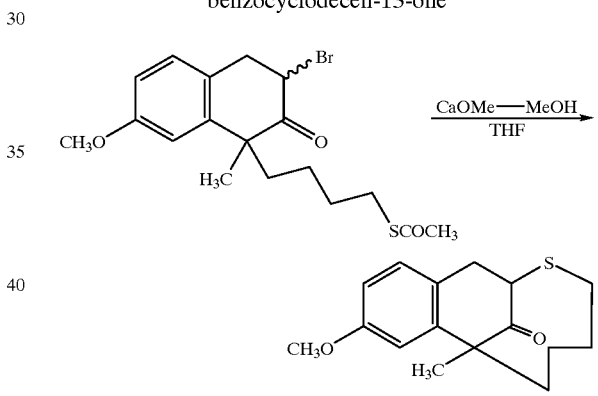

An epimeric mixture of 3-bromo-1-(4'-acetothiobutyl)-1-methyl-7-methoxy-2-tetralone (approximately 6.25 mmol) was dried via azeotropic distillation of toluene and dissolved in dry THF (200 ml), Lithium Bromide (dry, 0.54 g) was added, the solution was degassed with Ar at room temperature for one hour, and was cooled in an ice bath, well stirred, with a gentle flow of Ar passing through it. Sodium methoxide (0.5 M in Methanol, 13.75 ml) was dissolved in dry THF (75 ml), degassed with Ar at room temperature for one hour, after which it was added to the latter solution through a syringe pump over 4 hours. The combined reaction mixture was stirred for an additional ½ hour, diluted with ethylacetate (100 ml), washed with brine, dried over MgSO$_4$ and evaporated. The residue was purified on a silica gel column using a mixture of hexanes and ethylacetate (75:1, 50:1). The yield of product was approximately 50–55%. It solidified on standing.

$^1$H NMR (300 MHz, CDCl$_3$) δ: 1.4–1.95 (m, 4H); 2.85 (m, 2H); 2.7–3 (m, 2H); 3.4 (m, 1H); 3.82 (m, 4H); 6.7–7.1 (m, 3H) ppm. IR (film) 1693, 1609 cm$^{-1}$.

EXAMPLE 7

Preparation of epimeric 5,6,7,8,9,11,12 hepta hydro-3-methoxy-5-methyl-10-thia-5,11-methanobenzocyclodecen-13-oxime

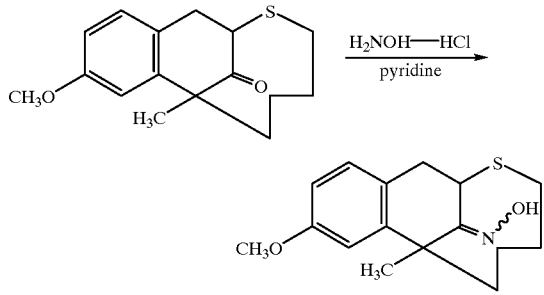

5,6,7,8,9,11,12-Heptahydro-3-methoxy-5-methyl-10-thia-5,11-methanobenzocyclodecen-13-one (1.32 g) was dried via azeotropic distillation of toluene, mixed with hydroxyl amine hydrochloride (2.64 g) and dry pyridine (5.2 ml) was added. Combined mixture was heated at 80° C. for 2 days. It was cooled, diluted with $CH_2Cl_2$ and washed with brine. After drying over $MgSO_4$, the solvent was evaporated off and the residue was purified on a silica gel column using a mixture of hexanes and ethylacetate (50:1, 25:1, 10:1, 5:1 2:1). The yield of the product was 1.22 g. (92%).

$^1$H NMR (300 MHz, $CDCl_3$) δ; 1.2–1.9 (m, 9H); 2.4 (m, 2H); 2.85 (m, 2H); 3.2 (dd, 1H); 3.8 (s, 3H); 5.11 (t, 1H); 6.6–7.1 (m, 3H) ppm. IR (film) 1609, 2200, 3250 cm$^{-1}$; Mass Spectrometry: m/z 292.

EXAXPLE 8

Preparation of 5,6,7,8,9,11,12-heptahydro-3-methoxy-5-methyl-10-thia-5,11-methano benzocyclodecen-13-hydroxylamine—Compound #8a and 5,6,7,8,9,11,12-heptahydro-3-methoxy-5-methyl-10-thia-5,11-methanobenzocyclodecen-13-amine-compound #8b

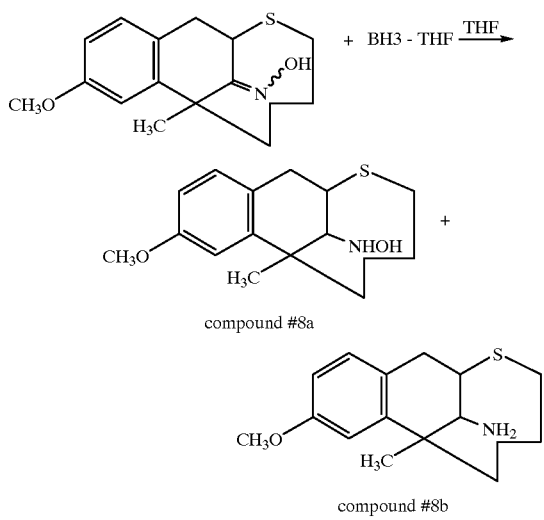

compound #8a compound #8b 5,6,7,8,9,11,12-Heptahydro-3-methoxy-5-methyl-10-thia-5,11-methanobenzocyclodecen-13-oxime (isomeric mixture, 0.3 g) was dried with toluene and dissolved in dry THF (30 ml). It was cooled in an ice bath under Ar atmosphere. Borane—THF complex (1M solution in THF, 7.87 ml) was added and the combined mixture was heated to reflux for 30 hours. It was cooled in an ice bath. Water (0.4 ml) and concentrated HCl (0.6 ml) were added carefully in respective order. The mixture was heated to reflux for 15 minutes, cooled and evaporated. The residue was basified with concentrated $NH_4OH$ to pH 12, extracted with $CH_2Cl_2$, washed with brine, dried over $MgSO_4$ and evaporated. The residue was purified on a silica gel column using a mixture of hexanes and ethylacetate (50:1, 20:1, 10:1, 5:1, 5:1.5, 2:1, 1:1 and 1:2). The yield of 5,6,7,8,9,11,12-heptahydro-3-methoxy-5-methyl-10-thia-5,11-methanobenzocyclodecen-13-hydroxylamine was 0.073 g (23.1%). It was crystallized from a mixture of ethylacetate and hexanes.

$^1$H NMR (300 MHz, $CDCl_3$) δ: 1.1–1.91 (m, 9H); 2.3 (m, 2H); 3.30 (d, 1H); 3.37 (m, 2H); 3.7 (m, 1H), 3.78 (s, 3H), 6.6–7.1 (m, 3H) ppm. IR (film): 1612, 3300 cm$^{-1}$; Mass Spectrometry: 293.8, 275.8, 260.8.

The structure of #8a was confirmed by single crystal X-ray crystallography.

The yield of 5,6,7,8,9,11,12-heptahydro-3-methoxy-5-methyl-10-thia-5,11-methanobenzocyclodecen-13-amine was 0.0968 g. (32%). The free base was soluble in hexanes.

$^1$H NMR (300 MHz, $CDCl_3$) δ: 0.8–2.5 (m, 11H), 3.18 (m, 3H), 3.6 (q, 1H), 3.8 (s, 3H) 6.6–7.1 (m, 3H) ppm.

This product was dissolved in ether (40 ml) and acidified with Methanol-HCl. The suspension was allowed to settle and filtered. The precipitate was washed with ether and dried, yielding 0.090 g of product.

$^1$H NMR (300 MHz, $CDCl_3$) δ: 0.8–1.7 (m, 6H); 1.8 (m, 2H); 2.0–2.5 (m, 3H); 3.45 (m, 2H); 3.5 (m, 2H); 3.8 (S, 3H) 6.7–7.1 (m, 3H) ppm. Mass Spectrometry: m/z 278.

EXAMPLE 9

Preparation of 5,6,7,8,9,11,12-heptahydro-3-hydroxy-5-methyl-10-thia-5,11 methanobenzocyclodecen-13-amine (sulphazocine) compound #9

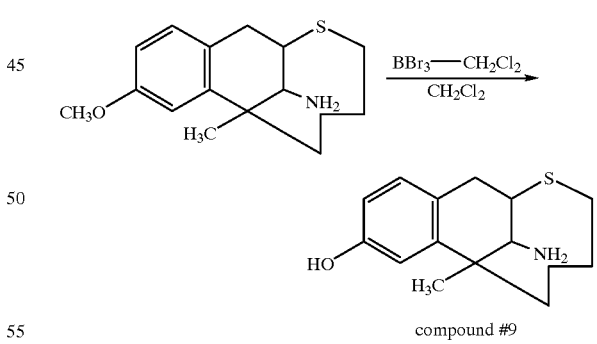

compound #9

5,6,7,8,9,11,12-Heptahydro-3-methoxy-5-methyl-10-thia-5,11-methanobenzocyclodecen-13-amine (0.260 g) was dried via azeotropic distillation of toluene and dissolved in dry $CH_2Cl_2$ (40 ml). It was cooled at −70° under Ar atmosphere. Boron tribromide solution (1M solution in $CH_2Cl_2$, 187 ml) was added and the combined mixture was allowed to stir at ambient temperature overnight. The reaction mixture was hydrolyzed with $NaHCO_3$, the pH lowered with $NH_4OH$ to 12, and extracted with $CH_2Cl_2$. The latter solution was dried over $MgSO_4$ and evaporated. The residue was purified on a silica gel column using a mixture of toluene and ethylacetate. (10:1, 5:1, 2:1, 1:1, 1:2).

The yield of 5,6,7,8,9,11,12-heptahydro-3-hydroxy-5-methyl-10-thia-5,11-methano benzocyclodecen-13-amine was 0.162 g (65%).

$^1$H NMR (350 MHz, DMSO-D$_6$) δ: 1.02 (m, 1H); 1.25 (m, 5H) 1.55 (m 2H); 2.01 (m, 2H); 2.55 (m, 1H); 2.97 (d, 1H) 3.08 (m, 1H), 3.14 (m, 2H); 6.4–6.9 (m, 3H) ppm.

The above product was converted to its hydrochloride form and purified via HPLC.

EXAMPLE 10

Preparation of 5,6,7,8,9,11,12-hepta hydro-3-hydroxy-5-methyl-10-thia-5,11-methanobenzocyclodecen-13-hydroxylamine compound #10

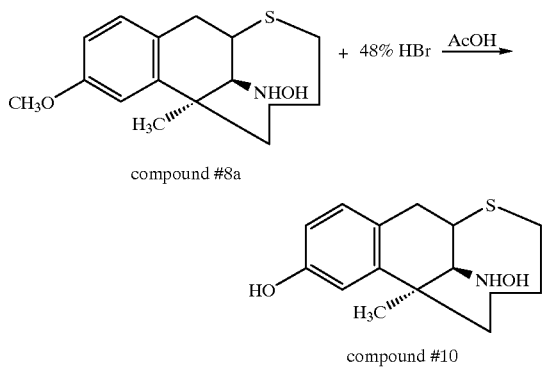

5,6,7,8,9,11,12-heptahydro-3-methoxy-5-methyl-10-thia-5,11-methanobenzoxycyclodecen-13-hydroxyl amine (0.166 g) was dissolved in a mixture of acetic acid (4.5 ml) and 48% HBr (4.5 ml). It was cooled, neutralized carefully with NaHCO$_3$ and extracted with CH$_2$Cl$_2$. Latter solution was washed with brine, dried over MgSO$_4$ and evaporated. The residue was purified on a silica gel column using a mixture of hexanes and ethylacetate (10:1, 10:1.5, 5:1). The yield of 5,6,7,8,9,11,12-heptahydro-3-hydroxy-5-methyl-10-thia-5,11-methanobenzocyclodecen-13-hydroxylamine was 0.035 g (22%).

$^1$H NMR (300 MHz, CDCl$_3$) δ: 1.1–1.91 (m, 9H); 2.30 (m, 2H); 3.28 (m, 1H), 3.34 (m, 2H); 3.7 (m, 1H), 6.6–7.0 (m, 3H) ppm.

Above product was converted to its hydrochloride form and purified by HPLC.

EXAMPLE 11

Preparation of compound #9a (−)-trans-5,6,7,8,9,11,12-heptahydro-10-thia-3-hydroxy-5-methyl-5,11-methanobenzocyclodecen-13-amine Compound #9 (2.96 g) was mixed with D-tartaric acid (2.01 g) dissolved in boiling ethanol (95%, 50 mL) and filtered. The insoluble mass was washed with hot ethanol (25 mL). Combined filtrates were evaporated to dryness and the residue was redissolved in hot ethanol (20 mL). A fluffy solid mass was collected and redissolved in hot ethanol (15 mL). Crystallization was allowed to proceed undisturbed at room temperature for 2 days. Semicrystalline mass was further subjected to similar fractional crystallization process two more times. A sample at this stage was found to have a diasteromeric purity of 98% via chiral derivatization with Marfey's reagent (0,267 g).

The tartrate salt of the title compound (0.1 g) was dissolved in hot methanol (20 mL) and transferred to a column packed with Amberlite IRA-400 (Cl$^-$ form) ion exchange resin (5 g, washed successively with methanol, water, 0.1M HCl, water and methanol). The column was washed with methanol (100 mL) and water (100 mL) in succession. Combined eluents were evaporated off and lyophilized. Residue (0.076 g)

EXAMPLE 12

Preparation of compound #9b (+)-trans-5,6,7,8,9,11,12-heptahydro-10-thia-3-hydroxy-5-methyl-5,11-methanobenzocyclodecen-13amine Compound #9-D-tartrate salt (highly enriched in dextrorotatory diastereomer 1.5 g) was mixed with NH$_4$OH (10 mL) saturated with sodium chloride and extracted with methylene chloride. The latter was washed with brine, dried over MgSO$_4$ and evaporated. Residue (1.27 g) was mixed with L-tartaric acid (0.87 g) and boiled with ethanol (95%, 100 mL) filtered, the filtrate then being allowed to crystallize at room temperature for 2 days. The precipitated mass was allowed to crystallize slowly from hot isopropanol. A sample was found to have a diastereomeric purity of 97% via chiral derivatization with Marfey's reagent to give 0.1515 g yield.

The tartrate salt of the title compound (0.076 g) was dissolved in hot methanol (25 mL) and transferred to a column packed with activated Amberlite IRA-400 (Cl$^-$ form, 5 g) which was then washed with methanol (100 mL) and water (100 mL) successively. Combined filtrates were evaporated and lyophilized residue (0.058 g)

EXAMPLE 13

Preparation of compound #11 trans-5,6,7,8,9,11,12-heptahydro-10-thia-3-hydroxy-5-methyl-5,11-methanobenzocyclodecen-13-guanidine

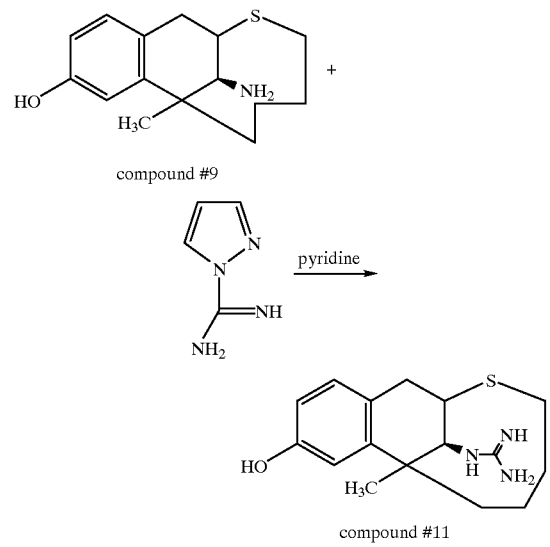

Compound #9 (0.35 g) was dried via azeotropic distillation with toluene and dissolved in dry pyridine (5 mL). 1H-pyrazole-1-carboxamidine hydrochloride (1.29 g) and diisopropyl ethylamine (1.74 mL) was added. Combined mixture was heated at 80° C. under nitrogen atmosphere for 4 days. Solvent was evaporated off and the residue was purified on a silica gel column using a mixture of methylene chloride and methanol. The product (0.41 g) was dissolved in methanol saturated with hydrogen chloride (5 mL) and the solvent evaporated off. The residue was purified by HPLC yielding 0.045 g final product.

EXAMPLE 14

Preparation of compound #12 trans-5,6,7,8,9,11,12-heptahydro-10-sulphono-3-hydroxy-5-methyl-5,11-methanobenzocyclo-decen-13-amine

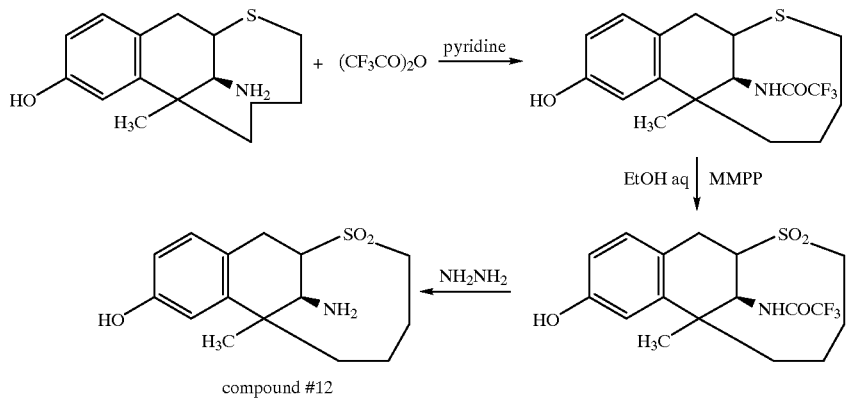

compound #12

Compound #9 (0.1 g) was dried via azeotropic distillation of toluene, dissolved in dry methylene chloride (20 mL) and cooled in an ice bath under Ar atmosphere. Trifluoroacetic anhydride (0.54 mL) and pyridine (0.5 mL) were added. After stirring at room temperature overnight the reaction mixture was hydrolyzed with aqueous solution of sodium bicarbonate, extracted with methylene chloride, washed with brine, dried over $MgSO_4$ and evaporated. Residue was purified on a silica gel column using a mixture of hexanes and methylene chloride to yield 0.068 g of trans-5,6,7,8,9,11,12-heptahydro-10-thia-3-hydroxy-5-methyl-5,11-methanobenzocyclodecen-13-trifluoroacetamide.

Trans-5,6,7,8,9,11,12-heptahydro-10-thia-3-hydroxy-5-methyl-5,11-methanobenzocyclodecen-13-trifluoroacetamide was dissolved in a mixture of ethanol (2 mL) and water (1 mL) and then cooled in an ice bath. Monoperoxyphthalic acid, magnesium salt hexahydrate (0.21 g) was added. After 1 hour aqueous saturated sodium bicarbonate (5 mL) was added. Combined mixture was stirred at room temperature overnight and evaporated off and the residue extracted with methylene chloride. The latter solution was washed with brine and evaporated yielding 0.123 g trans-5,6,7,8,9,11,12-heptahydro-10-sulphono-3-hydroxy-5-methyl-5,11-methanobenzocyclodecen-13-trifluoroacetamide.

Trans-5,6,7,8,9,11,12-heptahydro-10-sulphono-3-hydroxy-5-methyl-5,11-methanobenzocyclodecen-13-trifluoroacetamide (0.123 g) was dried via azeotropic distillation with toluene and anhydrous hydrazine (2 mL) was added. The mixture was stirred at room temperature for 2 days then evaporated and dried under vacuum. The product mixture was dissolved in methanol (2 mL) and allowed to stand at room temperature. Crystalline material (0.0372 g) was filtered out and dissolved in saturated solution of hydrogen chloride in methanol (2 mL) and then evaporated off. The residue was lyophilized yielding 0.031 g of the title compound.

ACTIVITY STUDIES:

Antinociceptive activity of compounds of the invention was determined in vivo in a PBQ writhing model and in the hot plate test in rodents. Inhibition of PBQ (phenyl-ρ-benzoquinone) induced writhing in mice is an assessment of both central and peripherally-mediated analgesia. For experimental protocol see Sigmund et al., *Proc. Soc. Ex. Biol. Med.*, 95, p. 729 (1957) which is incorporated herein by reference. Centrally-mediated analgesia was determined by the inhibition of a hot plate response in mice. For experimental protocol see G. Woolfe and A. Macdonald, *J. Pharmacol. Exp. Ther.*, 80, p. 300 (1994) which is incorporated herein by reference. Assays measuring opioid receptor binding affinities for $\mu$, $\delta$ and $\kappa$ receptors as well as GPI and MVD assays were determined through experimental protocol set out in Schiller et al., *Biophys. Res. Commun.*, 85, p. 1322 (1975); Rothman et al, Peptides, Vol 11, pp 311–331, 1990; Kaffa et al, Peptides 15(3), 401–404, 1994; Fowler et al, Neurochem. Int 24(5), 401–426, 1994; and Leslie F., Pharmacological Review 39(3), 197–249, 1987 incorporated herein by reference.

EXAMPLE 15

Radio Receptor Binding Assay

A. Membrane Preparation

Male Sprague-Dawley rats weighing between 350–450 g were sacrificed by inhalation of $CO_2$. The rats were decapitated and the brains minus cerebellum were removed and placed in ice-cold saline solution and then homogenized in ice-cold 50 MM Tris buffer pH 7.4 (10 ml/brain). The membranes were centrifuged at 14000 rpm for 30 min. at 4° C. The pellets were re-suspended in approximately 6 ml/brain of ice-cold Tris buffer 50 mM pH 7.4 and stored at −78° C. until ready for use. Protein quantification of the brain homogenate was conducted according to the protein assay kit purchased from Bio-Rad.

B. Radioligand Assay ($^3$H)-DAMGO and ($^3$H) DADLE were used as radioligands for the $\mu$ and $\delta$ receptors, respectively. Radioligand 50 $\mu$l, membranes 100 $\mu$l and serially diluted test compound were incubated for 1 hr at 22° C. Non specific binding was determined using 500 fold excess of unlabeled ligand in the presence of tracer and membranes. Free ligand was separated from bound by filtration through Whatman GF/B paper (presoaked in polyethylenimine 1% aqueous solution) and rinsing with ice-cold 50 mM Tris pH 7 4 using a Brandel cell harvester. The filters were dried and radioactivity was counted in a 24 well microplate in the presence of 500 ml scintillant per well. Radioactivity was measured using a Wallac 1450 Microbeta counter.

Displacement curves were drawn using Microsoft Excel program. The Ki's for the various compounds were determined from the $IC_{50}$ according to the Cheng and Prusoff equation.

EXAXPLE 16

Phenylquinone Writhing Assay

A. Subjects

The test was performed using CD #1 male mice (Charles River) weighing between 19 and 25 g. Animals were maintained in constant conditions of light, temperature and humidity. The animals were acclimatized for three days prior to experimentation.

B. Drug Preparation and Dosage Procedure

A solution of phenylquinone (0.02%) was prepared in the following fashion. 20 mg of phenylquinone was dissolved in 5 ml ethanol 90%. The phenylquinone solution was slowly added to 95 ml of distilled water with continuous stirring and gentle heating. The phenylquinone solution was protected from light at all times and a new solution was prepared every day for the test. It is recommended to wait 2 hours before using the phenylquinone solution.

All test compounds were dissolved in distilled water and administered subcutaneously or by oral gavage.

Mice were injected, by intraperitoneal route, with a solution of 0.02% phenylquinone (2-phenyl-1,4-benzoquinone, Sigma). The phenylquinone was injected at various time intervals of 20, 60, 120 and 180 minutes after administration of the compound (or vehicle, or standard).

EXAMPLE 17

Hot Plate Assay in mice

A. Subjects

For this test, CD #1 male mice (Charles River) weighing between 20–25 grams were used. The mice were weighed, identified, and randomized into groups of 10.

B. Drug Preparation and Injection Protocol

The mice were usually treated by subcutaneous injection of the compound (or the standard or vehicle) or by oral gavage.

C. Measurement of Analgesic Activity

The mice were evaluated individually for a latency reaction time on the hot plate. The temperature of the hot plate (Sorel, model DS37) was set at 55° C. The mice were observed for signs of discomfort such as licking or shaking of the paws, attempting to escape (jumping off the plate) or trembling. The reaction time was recorded when one of these signs was noted. The cut off for latency response was 15 seconds so as to prevent damage to the paw tissue. For the determination of analgesic time course the mice were observed at different time intervals following administration of the compound (or vehicle, or standard). The time intervals are typically 30, 60 or 120 minutes (or other).

For each time reading, the average reaction time of the control group was multiplied by 1.5. The reaction time of each treated animal was compared to the "control average× 1.5". If the reaction time was inferior to the "control average×1.5", the mouse was considered not to have had an analgesic effect. If the reaction time was superior to the "control average×1.5" then the mouse was considered to have had an analgesic effect. If the percentage of mice rendered analgesic was less than 30%, the compound was considered inactive.

Figure 2:
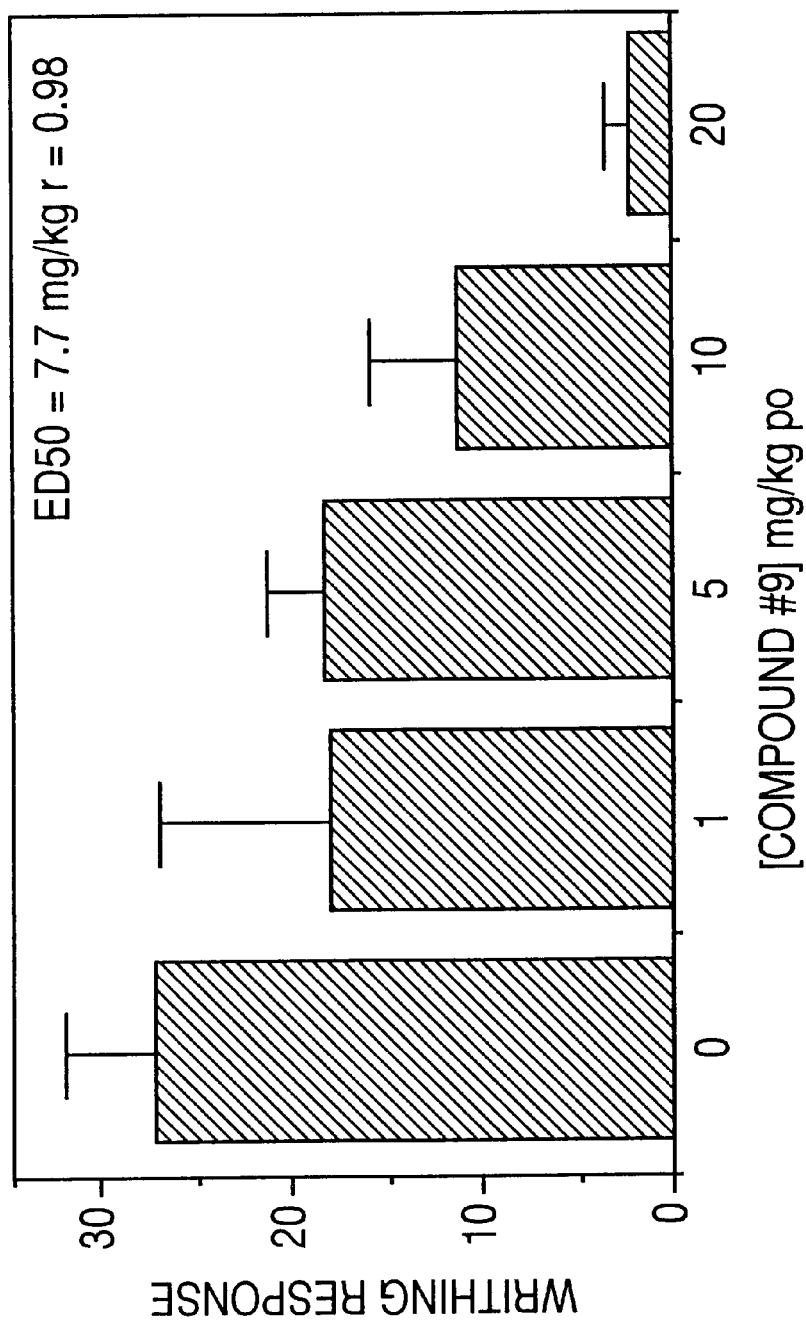
FIG. 2 shows dose dependent inhibition of the writhing response (PBQ) by compound #9 administered orally to mice.

FIGS. 1–3 show the antinociceptive effects of compound #9 in mice by evaluating the reaction of the mice in the hot plate test and inhibition of the writhing response in the PBQ assay.

As shown in FIG. 1, after 15 minutes, the latency response time of the mice treated with 2.5 mg/kg of compound #9 is almost maximum. The reaction time of the mice treated with 5 mg/kg of compound #9 is about 19 seconds compared to a control value of approximately 7 seconds. These results indicate that compound #9 does elicit a dose dependent latency response to radiant heat.

FIG. 2 shows the inhibition of the writhing response elicited in mice by oral administration of compound #9 one hour prior to PBQ administration FIG. 3 demonstrates inhibition of the writhing response elicited in mice by s.c. administration of compound #9, twenty minutes prior to PBQ administration.

In both figures, a dose-dependent inhibition of writhing response was observed for of compound #9 both by the oral and sub-cutaneous route.

We claim:

1. A compound of formula (I):

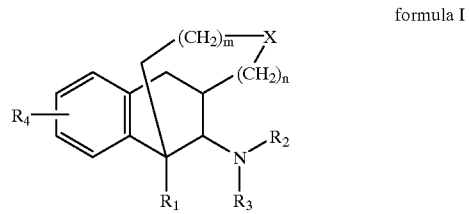

formula I wherein $R_1$ is H, $C_{1-6}$ alkyl, or $C_{6-12}$ aryl optionally substituted with polar groups;

$R_2$ and $R_3$ are independently H, OH, $C_{1-6}$ alkyl, —C(NH)—$NH_2$, a positively charged group, or $C_{7-13}$ aralkyl optionally substituted with $NH_2$, OH, $C_{1-6}$ alkyl, or halogen; or $R_2$ and $R_3$ together form a 5 to 6 member ring optionally incorporating a heteroatom;

$R_4$ is H, $C_{1-6}$ alkyl, $OR_6$, $SR_6$ or $N(R_6)_2$, wherein each $R_6$ is independently H, $C_{1-3}$ alkyl;

X is S, SO, or $SO_2$;

n is an integer from 0 to 2;

m is an integer from 1 to 3.

2. A comund according to claim 1, wherein X is selected from S and $SO_2$, m is 3 and n is 0.

3. A compound according to claim 2, wherein X is S.

4. A compound according to claim 3, wherein $R_2$ is H and $R_3$ is selected from H, OH and —C(NH)—$NH_2$.

5. A compound according to claim 3, wherein $R_1$ is methyl.

6. A compound according to claim 3, wherein $R_4$ is selected from OH and methoxy.

7. A compound according to claim 6, wherein $R_4$ is OH.

8. A compound according to claim 1, selected from:

8b 5,6,7,8,9,11,12-heptahydro-3-methoxy-5-methyl-10-thia-5,11-methanobenmocyclodecene-13-amine;

9 5,6,7,8,9,11,12-heptahydro-3-hydroxy-5-metyl-10-thia-5,11-methanobenzocyclodecen-13-amine (sulphazocine);

10 5, 6,7,8,9,11,12-heptahydro-3-hydroxy-5-methyl-10-thia-5,11-methanobenzocyclodecene-13-hydroxylamine;

8a 5,6,7,8,9,11,12-hetahydro-3-methoxy-5-methyl-10-thia-5,11-methano benzocyclo-decen-13-hydroxylamine; #12 trans-5,6,7,8,9,11,12-heptahydro-10-sulphono-3-hydroxy-5-methyl-5,11-methanobenzocyclo-decen- 13-amine;

9a (−)-trans-5,6,7,8,9,11,12-heptahydro-10-thia-3-hydroxy-5-methyl-5,11-methanobezocyclodecen-13-amine; #9b (+)-trans-5,6,7,8,9,11,12-heptahydro-10-thia-3-hydroxy-5-methyl-5,11-methanobenzocyclodecen-13amine; and

11 trans-5,6,7,8,9,11,12-heptahydro-10-thia-3-hydroxy-5-methyl-5,11-methanobenzocyclodecen-13-guanidine;

12 trans-5,6,7,8,9,11,12-heptahydro-10-sulphono-3-hydroxy-5-methyl-5,11-methanobenzocyclo-decen-13-amine.

9. A compound according to claim 1, selected from:

9 5,6,7,8,9,11,12-heptahydro-3-hydroxy-5-methyl-10-thia-5,11-methanobenzocyclo-decen-13-amine (sulphazocine); and

9a (−)-trans-5,6,7,8,9,11,12-heptahydro-10-thia-3-hydroxy-5-methyl-5,11-methanobenzocyclodecen-13-amine.

10. A method of inducing analgesia in a mammal comprising administering to said mammal a pharmaceutically effective amount of a compound according to formula (I):

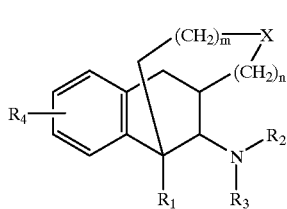

formula I wherein

R₁ is H, C$_{1-6}$ alkyl, or C$_{6-12}$ aryl optionally substituted with polar groups;

R₂ and R₃ are independently H, OH, C$_{1-6}$ alkyl, —C(NH)—NH₂, a positively charged group, or C$_{7-13}$ aralkyl optionally substituted with NH₂, OH, C$_{1-6}$ alkyl, or halogen; or R₂ and R₃ together form a 5 to 6 member ring optionally incorporating a heteroatom;

R₄ is H, C$_{1-6}$ alkyl, OR₆, SR₆ or N(R₆)₂, wherein each R₆ is independently H, C$_{1-3}$ alkyl;

X is S, SO, or SO₂;

n is an integer from 0 to 2;

m is an integer from 1 to 3.

11. The method according to claim 10, wherein X is selected from S and SO₂, m is 3 and n is 0.

12. The method according to claim 11, wherein, wherein X is S.

13. The method according to claim 10, wherein R₂ is H and R₃ is selected from H, OH and —C(NH)—NH₂.

14. The method according to claim 10, wherein R₁ is methyl and R₄ is OH.

15. The method according to claim 10, wherein said compound is selected from:

8b 5,6,7,8,9,11,12-heptahydro-3-methoxy-5-methyl-10-thia-5,11-methanobenzocyclodecene-13-amine;

9 5,6,7,8,9,11,12-heptahydro-3-hydroxy-5-methyl-10-thia-5,11-methanobenzocyclodecen-13-amine (sulphazocine);

10 5,6,7,8,9,11,12-heptahydro-3-hydroxy-5-methyl-10-thia-5,11-methanobenzocyclodecene-13-hydroxylamine;

8a 5,6,7,8,9,11,12-heptahydro-3-methoxy-5-methyl-10-thia-5,11-methano benzocyclo-decen-13-hydroxylamine; #12 trans-5,6,7,8,9,11,12-heptahydro-10-sulphono-3-hydroxy-5-methyl-5,11-methanobenzocyclo-decen-13-amine; #9a (−)-trans-5,6,7,8,9,11,12-heptahydro-10-thia-3-hydroxy-5-methyl-5,11-methanobenzocyclodecen-13-amine;

9b (+)-trans-5,6,7,8,9,11,12-heptahydro-10-thia-3-hydroxy-5-methyl-5,11-methanobenzocyclodecen-13-amine; and

11 trans-5,6,7,8,9,11,12-heptahydro-10-thia-3-hydroxy-5-methyl-5,11-methanobenzocyclodecen-13-guanidine;

12 trans-5,6,7,8,9,11,12-heptahydro-10-sulphono-3-hydroxy-5-methyl-5,11-methanobenzocyclo-decen-13-amine.

16. A method of activating opioid receptors in a mammal comprising administering to said mammal an opioid receptor activating amount of a compound according to formula (I):

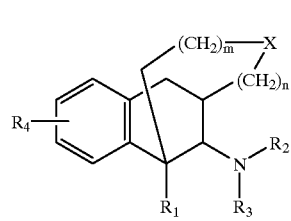

formula I wherein

R₁ is H, C$_{1-6}$ alkyl, or C$_{6-12}$ aryl optionally substituted with polar groups;

R₂ and R₃ are independently H, OH, C$_{1-6}$ alkyl, —C(NH)—NH₂, a positively charged group, or C$_{7-13}$ aralkyl optionally substituted with NH₂, OH, C$_{1-6}$ alkyl, or halogen; or R₂ and R₃ together form a 5 to 6 member ring optionally incorporating a heteroatom;

R₄ is H, C$_{1-6}$ alkyl, OR₆, SR₆ or N(R₆)₂, wherein each R₆ is independently H, C$_{1-3}$ alkyl;

X is S, SO, or SO₂;

n is an integer from 0 to 2;

m is an integer from 1 to 3.

17. The method according to claim 16, wherein X is selected from S and SO₂, m is 3 and n is 0.

18. The method according to claim 16, wherein R₂ is H and R₃ is selected from H, OH and —C(NH)—NH₂.

19. The method according to claim 16, wherein R₁ is methyl and R₄ is OH.

20. The method according to claim 16, wherein said compound is selected from:

8b 5,6,7,8,9,11,12-heptahydro-3-methoxy-5-methyl-10-thia-5,11-methanobenzocyclodecene-13-amine;

9 5,6,7,8,9,11,12-heptahydro-3-hydroxy-5-methyl-10-thia-5,11-methanobenzocyclodecen-13-amine (sulphazocine);

10 5,6,7,8,9,11,12-heptahydro-3-hydroxy-5-methyl-10-thia-5,11-methanobenzocyclodecene-13-hydroxylamine;

8a 5,6,7,8,9,11,12-heptahydro-3-methoxy-5-methyl-10-thia-5,11-methano benzocyclo-decen-13-hydroxylamine; #12 trans-5,6,7,8,9,11,12-heptahydro-10-sulphono-3-hydroxy-5-methyl-5,11-methanobenzacyclo-decen-13-amine; #9a (−)-trans-5,6,7,8,9,11,12-heptahydro-10-thia-3-hydroxy-5-methyl-5,11-methanobenzocyclodecen-13-amine;

9b (+)-trans-5,6,7,8,9,11,12-heptahydro-10-thia-3-hydroxy-5-methyl-5,11-methanobenzocyclodecen-13-amine; and

11 trans-5,6,7,8,9,11,12-heptahydro-10-thia-3-hydroxy-5-methyl-5,11-methanobenzocyclodecen-13-guanidine;

12 trans-5,6,7,8,9,11,12-heptahydro-10-sulphono-3-hydroxy-5-methyl-5,11-methanobenzocyclo-decen-13-amine.

* * * * *